(12) United States Patent
Mack

(10) Patent No.: US 7,589,836 B2
(45) Date of Patent: Sep. 15, 2009

(54) OPTOELECTRONIC SENSOR DEVICE

(75) Inventor: Bernd Mack, Remshalden (DE)

(73) Assignee: odelo GmbH, Schwaikheim (DE)

( * ) Notice: Subject to any disclaimer, the term of this patent is extended or adjusted under 35 U.S.C. 154(b) by 49 days.

(21) Appl. No.: 12/052,915

(22) Filed: Mar. 21, 2008

(65) Prior Publication Data

US 2008/0231847 A1 Sep. 25, 2008

(30) Foreign Application Priority Data

Mar. 22, 2007 (DE) .................. 10 2007 013 688

(51) Int. Cl.
G01N 21/00 (2006.01)

(52) U.S. Cl. .............. 356/239.8; 250/227.25; 318/483

(58) Field of Classification Search ... 356/237.1–237.5, 356/239.7, 239.8; 250/573–574, 227.24, 250/227.25; 318/119, 140, 34, 483, 806
See application file for complete search history.

(56) References Cited

U.S. PATENT DOCUMENTS

| | | | | |
|---|---|---|---|---|
| 5,276,388 A | * | 1/1994 | Levers | 318/444 |
| 5,323,637 A | * | 6/1994 | Bendicks et al. | 73/29.01 |
| 5,483,346 A | * | 1/1996 | Butzer | 356/369 |
| 5,498,866 A | * | 3/1996 | Bendicks et al. | 250/227.25 |
| 6,097,167 A | * | 8/2000 | Tanaka et al. | 318/483 |
| 7,518,098 B2 | * | 4/2009 | Mack | 250/221 |
| 2002/0131046 A1 | * | 9/2002 | Christy et al. | 356/445 |
| 2008/0105837 A1 | * | 5/2008 | Mack | 250/564 |

FOREIGN PATENT DOCUMENTS

| | | |
|---|---|---|
| DE | 10 2004 007 957 A1 | 9/2005 |
| EP | 1 087 221 A1 | 3/2001 |

* cited by examiner

Primary Examiner—Hoa Q Pham
(74) Attorney, Agent, or Firm—Reising Ethington P.C.

(57) ABSTRACT

An optoelectronic sensor device is described for recording of soiling on a transparent cover, with at least one light source that emits at least two light beams, a test surface arranged in the cover, having a concave surface exposed to environmental effects, through which the light beams emerge and reenter, as well as at least one receiver that measure the radiation powers of the light beams, on which the light beams are imaged independently of each other after reentry. The test surface has at least two areas with different microstructurings, in which a first microstructuring is designed, so that a liquid applied to the area provided with the first microstructuring is held together drop-like, and a second microstructuring is designed, so that a liquid applied to the area provided with the second microstructuring is distributed film-like, in which at least a first light beam emerges and reenters through the first area and at least a second light beam emerges and reenters through the second area, so that by comparison of the radiation powers of the two light beams, a conclusion can be drawn concerning the transparency of the cover exposed to soiling. In addition a method is described for determination of the transparency of soiling by a transparent surface exposed to environmental effects.

15 Claims, 1 Drawing Sheet

OPTOELECTRONIC SENSOR DEVICE

Figure 1:
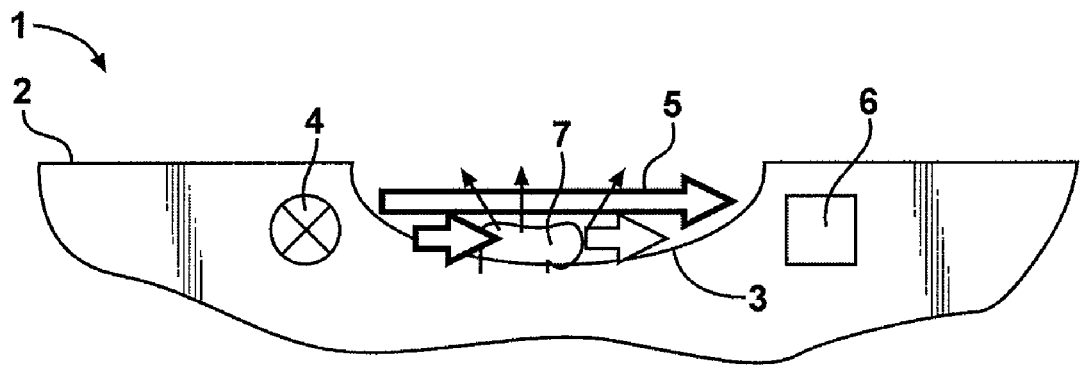

The invention concerns an optoelectronic sensor device applicable for indirect recording of transparency of a surface exposed to soiling by environmental effects, especially a transparent cover, like a pane of glass. The invention also concerns a method for detecting whether a transmission surface is soiled.

A number of optoelectronic sensors are known to record soiling, for example, rain, snow, moisture, slush, dust and the like, of a surface of a transparent cover exposed to environmental effects, like a windshield, headlight cover, light cover or a lens or protective cover of a camera system or the like.

A first known measurement principle of such optoelectronic sensors is based on reflection of light on the outer surface of the cover forming an optical interface between media with different refractive indices exposed to environmental effects. For example, in rain sensors that control an automatic drive of vehicle windshield wipers, a light beam is emitted at a flat angle of incidence into the windshield and reflected back to a sensor according to the laws of optics, with an outlet angle that corresponds to the angle of incidence from the optical interface between the glass and air. If soiling occurs through optically transparent media, like water, light is coupled outward from the windshield and the light intensity measured in the receiver is reduced. If soiling occurs through optically nontransparent media, like dust, the reflection properties of the optical interface also change, and light is also absorbed in the dust, so that the light intensity measured in the receiver is also reduced.

A second known measurement principle operates according to the photoelectric beam principle. In this case, light passes through the surface of a transparent cover exposed to environmental effects once or several times before it impinges on a receiver. The degree of soiling can be determined by means of the known emitted luminous power and the actually received luminous power. In optically nontransparent media, like dust, the reduction in received light intensity is proportional to the soiling. In optically transparent media, like water or oil, the measured degree of soiling can vary strongly. For example, raindrops can act as optical elements and deflect the light beam used for measurement or couple it out from the prescribed beam path. Because of this, in the extreme case, no light impinges on the receiver, so that high soiling is determined.

An optoelectronic sensor device is known from EP 1 087 221 A1, which has a test surface that can be integrated in a cover. The test surface is designed concave and is part of a radiation conductor. The sensor device has two light sources that couple light beams or generally test light into the radiation conductor. The radiation conductor is designed, so that the test light emerges through the test surface, reenters it and is imaged on two receivers. The effect of coupling out of the test light by an individual raindrop on the measurement result is reduced by average value formation of the radiation powers measured in the two receivers.

In an optoelectronic sensor device used as a rain sensor, which controls an automatic drive of a windshield wiper, it has thus far been tolerated that driving of the windshield wiper occurs independently of the type of soiling and therefore independently of the adverse effect on transparency of the cover by the soiling.

According to the prior art, soiling from transparent liquids that do not influence the transparency of the surface could not be distinguished from the transparency of soiling from nontransparent liquids or solids that adversely affect the transparency of the surface.

For applications in which the transparency in the cover is significant when soiling occurs, this is not sufficient. Recording the actual transparency, for example, can be of interest for a transparent cover exposed to environmental effects, which is arranged in the beam path of an optoelectronic measurement device, in which the received light intensity serves as a measured quantity. As an example, a visibility measurement device for vehicles or solar intensity measurement device, which can be mounted, for example, behind the windshield or other transparent cover in or on the auto body of a vehicle, can be mentioned. Recording reduced transparency can also be of interest to guarantee visibility of lit vehicle lights from a certain distance, in order to correspondingly adjust their luminous power, for example.

One task of the invention is to provide an optoelectronic sensor device, with which the transparency of soiling of a cover exposed to environmental effects can be determined, as well as a method for determination of the transparency of a surface exposed to soiling by environmental effects.

This task is solved by the features of Claim 1 and the features of Claim 9.

The first object of the invention therefore concerns an optoelectronic sensor device to record soiling on a transparent cover for a specified wavelength range of electromagnetic waves, with at least one light source that emits at least two light beams in the corresponding wavelength range, a test surface arranged in the cover, having a concave surface exposed to environmental effects, through which the light beams emerge and, if no soiling is situated on the test surface, reenter, as well as at least one receiver that measures the radiation power of the light beam, on which the light beams are imaged independently of each other after their reentry. The optoelectronic sensor device according to the invention is characterized by the fact that the test surface has at least two areas with different microstructuring on its concave surface. A first microstructuring is designed so that a liquid applied to the area provided with the first microstructure is held together drop-like, because of its surface tension, and forms a drop, so that in the area of the first microstructuring, coupling out of the light beam occurs from soiling in the form of a liquid, optically transparent medium. A second microstructuring is designed so that a liquid applied to the area provided with the second microstructuring is distributed film-like, so that in the area of the second microstructuring, coupling out of a light beam is avoided by soiling in the form of a liquid optically transparent medium. The areas provided with different microstructures are arranged on the test surface, so that in the unsoiled state of the surface, at least a first light beam emerges and reenters through the first area and at least the second light beam through the second area. By evaluation, for example, by comparison of the radiation powers of the two light beams measured by the receiver or receivers, a conclusion can be drawn concerning the transparency of the cover exposed to soiling independently of whether the soiling is caused by transparent or nontransparent, liquid or solid media. The term light beam includes any type of electromagnetic waves that propagate beam-like according to the laws of optics. Semiconductor-based radiation sources are preferably used as light source, which emit light beams in a wavelength range appropriate for a specific application, for example, infrared light in the near-infrared range. Semiconductors are also preferably used as receivers, for example, PIN (positive intrinsic negative) diodes.

It is recognizable that the invention can be implemented in each case by a combination of smooth and structured surfaces of the test surface, through which light beams emerge and reenter separately, so that compensation for the error caused by transparent liquid drops is achieved. By separate evaluation of differently designed surfaces, a distinct error recognition of the problem case of water drops is possible. In smooth surfaces, a liquid applied to the surface is held together by its surface tension, so that drops are formed. Because of their optical properties, these couple out a light beam passing through it and produce a similar behavior to soiling caused by an optically nontransparent medium. The second microstructuring is designed, so that a liquid applied to it is pulled flat to a film, in which case no coupling out occurs through optically transparent media, so that by comparison of the light radiation powers of the light beams passing through the first and second microstructuring, a conclusion can be drawn concerning the transparency of the soiling and the effect of soiling on the transparency of the cover.

The term concave here includes any configuration in which the test surface has an area in cross-section that is offset relative to a surrounding area, in particular, is made to lie deeper, for example, a V-shaped indentation, a spherical recess or the like.

It is important to emphasize that the optoelectronic sensor device can also be integrated in nontransparent covers, in order to record soiling of such a cover through a nontransparent media. This can be used, for example, in applications that operate with electromagnetic waves lying outside the visible wavelength range, like RADAR (radio detection and ranging) sensors, which are adversely affected by soiling through nontransparent media, but need not necessarily be arranged behind transparent covers. Generally, the sensor device can utilize a light source that operates outside of the wavelength range visible to the human eye. The cover itself, as well as the test surface in such a case, must be transparent for the employed wavelength range, but need not necessarily be designed transparent for the range visible to the human eye, for example, during use of a light source that emits light beams in the infrared (IR) or ultraviolet (UV) range.

Appropriate microstructurings are known, for example, through WO 02/085520 A2. Small liquid amounts are described there for manipulation on surfaces of chips and similar microstructurings that can be wetted with different intensity by a liquid. Such microstructurings are, in principle, appropriate for use in the context of the present invention.

An advantageous embodiment of the optoelectronic sensor device proposes that the at least one light source that emits two light beams includes a device for beam widening and/or beam splitting, like optical elements, like prisms or partially transparent mirrors.

The optoelectronic sensor device can also have at least two light sources that each emit a light beam.

The at least one receiver that measures the radiation power of the light beams preferably includes a device for beam combination, for example, optical elements, like prisms or partially transparent mirrors, as well as means to distinguish the two light beams. The means to distinguish the two light beams can be means for time-offset emission of the two light beams, for example. Evaluation then preferably occurs in the time multiplex method. It is also conceivable to use different wave ranges and/or different polarization planes for the two light beams, in which the at least one receiver furnishes measurement signals distinguishable from each other as a function of wavelength range and/or polarization plane.

The optoelectronic sensor device, with particular preference, includes at least two receivers, on each of which a light beam is imaged.

The first microstructuring can be designed, for example, as a smooth, for example, polished or coated surface. The second microstructuring can be designed, for example, as a matted or roughened surface.

The second microstructuring is preferably produced by a fine surface structure beneath a drop size that forms on the material of the test surface ordinarily in liquid drops. Fine structures below ordinary drop sizes prevent drop formation, so that the liquid runs widely in the structures designed, for example, as recesses, and smooth the surface structure. Because of this, coupling out of light beams on the areas of the test surface provided with the second microstructuring is avoided. The fine surface structure preferably matches the appearance of the optoelectronic sensor device in the appearance of the surroundings formed by the cover. Advantageously, by using a logo or inscription in the structure, or a continuation of the surrounding appearance in the surface structure, for example, in a vehicle, lights of the optical structure or reflective structure as outer grooves or honeycomb structure. Partial surfaces can then also have structures larger than ordinary drop sizes.

According to a particularly advantageous embodiment of the optoelectronic sensor device, the first microstructuring is produced by a hydrophobic nanostructure and the second microstructuring by a hydrophilic nanostructure. Hydrophobic and hydrophilic nanostructures can be produced much more durable and are not subject to continuous slow degeneration of their surface properties, like smooth and rough surfaces, for example, polished surfaces that become blunt with time or matted surfaces that become reflecting over time.

The microstructurings can be produced, for example, by at least partial coating of the test surface. Coating is a tested and cost-effective means to obtain the desired microstructuring.

The microstructurings can also be produced by at least partially embossing of fine surface structures. It is conceivable here to emboss logos, symbols, material designations or codes and the like as microstructuring.

The test surface is preferably an integral component of the cover. Because of this, no defect sites form between the cover and the test surface, which might adversely affect the operational reliability of the optoelectronic sensor device, for example, by entry of liquids.

As an alternative, the test surface can be a radiation conductor integrated in the cover. Because of this, the optoelectronic sensor device can be produced as a mass-produced product cost-effectively, independently of the cover. In addition, integration in optically nontransparent covers is also conceivable, for example, in order to be able to record the soiling of the surface through optically nontransparent media.

A second object of the invention concerns a method for determination of the transparency of soiling of a surface transparent to electromagnetic waves of a certain wavelength range and exposed to environmental effects. The method includes process steps:

Arrangement of at least two areas provided with different microstructurings on the surface, a first microstructuring being designed so that a liquid applied to the area provided with the first microstructuring is held drop-like by its surface tension and forms drops, and a second microstructuring being designed so that a liquid drop applied to the area provided with the second microstructuring is distributed to a liquid film, Generation of at least two light beams with a wavelength within a certain wavelength range, at least a first one of which emerges through the first area and reenters, and at least a second one of which emerges through the second area and reenters in the unsoiled state of the surface, Measurement of the radiation power of the light beams (10, 11) independently of each other, as well as Evaluation of the radiation powers of the two light beams, in which the result of evaluation is an unsoiled surface, if radiation powers are measured for both light beams that are essentially unchanged relative to the assigned starting values in the unsoiled state, and the result of the evaluation is a surface wetted by a transparent liquid, if, for the first light beam, a radiation power reduced relative to the assigned starting value is measured and, for the second light beam, a higher radiation power relative to the corresponding start value is measured.

For example, by establishing a threshold value for a radiation power of the light beams, above which the surface is considered unsoiled, measurement of the radiation powers of the light beams that emerge and reenter the areas provided with the different microstructuring independently of each other, and evaluation of the radiation powers of the two light beams, a conclusion can be drawn concerning the transparency of the surface with limited demands, in which the result of the evaluation is a soiled surface not transparent for the employed wavelength range, if both radiation powers lie below the threshold value, the result of a comparison is a wetted surface transparent for the employed wavelength range, if the radiation power of the light beam emerging and reentering the area provided with the first microstructuring lies below the threshold value and the radiation power of the light beam that emerges and reenters the area provided with the second microstructuring or lies above the threshold value, and the result of the evaluation is an unwetted surface transparent for the employed wavelength range, when both radiation powers lie above the threshold value.

A degree of transparency of the surface can be determined by independent comparison of the radiation powers of the two light beams with characteristics that apply for the corresponding areas. Thus, during soiling of the surface with, say, rainwater, the radiation power of the first light beam diminishes continuously, whereas the radiation power of the second light beam increases at least at the beginning of wetting. The radiation power of the first light beam continuously diminishes from clean liquids that do not influence transparency and the radiation power of the second light beam increases. Both radiation powers continuously diminish from solid dirt particles. These properties can be utilized to determine the degree of soiling of the surface by means of characteristics determined by laboratory experiments with reference to the measured radiation powers.

The method is preferably modified so that a conclusion can be drawn concerning soiling of a cover connected to the surface by determination of the soiling or transparency of the surface.

The invention is further explained below by means of a practical example and with reference to the drawings.

Figure 2:
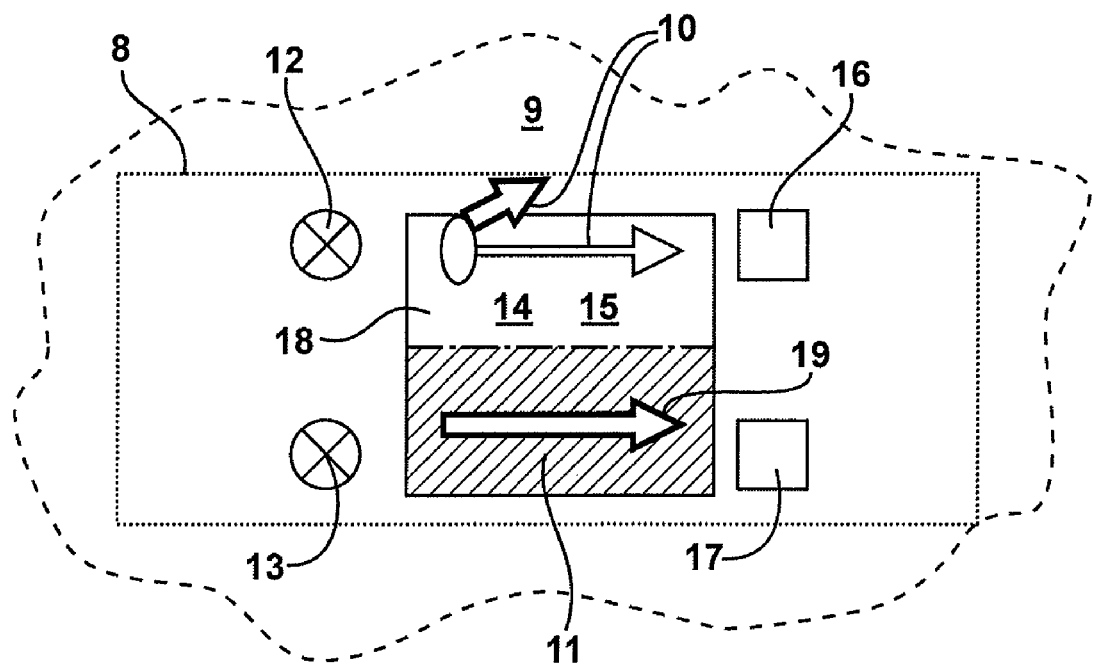

In the drawings:

FIG. 1 shows a schematic view of the method of operation of an optoelectronic sensor device according to the prior art in a side view, as well as FIG. 2 shows a schematic view of the method of operation of an optoelectronic sensor device according to the invention in a top view.

FIG. 1 shows an optoelectronic sensor device 01, which has a test surface 03 integrated in a cover 02. The test surface 03 is designed concave. The sensor device 01 has a light source 04, which emits light beams 05. The light beams 05 emerge through the test surface 03 and reenter it again and are imaged on receiver 06. A raindrop 07 situated on test surface 03 couples out the light beams 05 partially and scatters their luminous power into the environment. Because of this, the radiation power measured by receiver 07 is reduced and, although the transparency of cover 02 and test surface 03 is not adversely affected by raindrop 07, soiling is measured.

An optoelectronic sensor device 08 depicted in FIG. 2 for recording of soiling on a transparent cover 09 has two light sources 12, 13 that each emit a light beam 10, 11, a test surface 15 arranged in cover 09 and having a concave surface 14 exposed to environmental effects, through which the light beams 10, 11 emerge and reenter at least in the unsoiled state of surface 14. In addition, the optoelectronic sensor device 08 includes two receivers 16, 17 that measure the radiation powers of light beams 10, 11, on which the light beams 10, 11 are imaged independently of each other after reentry. The test surface 15 of the optoelectronic sensor device 08 has two areas 18, 19 on its concave surface with different microstructurings. A first microstructuring is designed, so that a liquid applied to the area 18 provided with the first microstructuring is held together drop-like by its surface tension and a drop is formed, so that coupling out of the light beam 10 occurs in area 18 of the first microstructuring through an optically transparent medium. A second microstructuring is designed, so that a liquid applied to the area 18 provided with the second microstructuring is distributed film-like, so that coupling out of a light beam 11 is avoided in area 19 of the second microstructuring through an optically transparent medium. The areas 18, 19 provided with the different microstructurings are arranged on the test surface 15, so that in the unsoiled state of the surface, the first light beam 10 emerges and reenters through the first area 18 and the second light beam 11 emerges and reenters through the second area 19. By comparison of the radiation powers of the two light beams 10, 11, measured by the receiver 16, 17, a conclusion can be drawn concerning the transparency of the cover 09 exposed to soiling, independently of whether the soiling is caused by a solid or liquid media.

The desired different microstructures can be designed, for example, by a structured outside surface arranged in the second area 19 of the test surface 15 serving as second microstructuring, similar to a finely structured Fresnel lens, parallel grooves or a honeycomb pattern, similar to a reflector, and by a smooth surface arranged in the first area 18 of the test surface 15 serving as first microstructuring. Such microstructurings change the appearance of rear lights, for example, of a vehicle, only slightly or not at all.

It is important to emphasize that the microstructurings are designed, so that they are preserved over the entire lifetime of the vehicle without losing their properties. This is possible, in particular, by designing the microstructurings as nanostructures or by forming the microstructurings in the form of structures in the millimeter range.

The invention claimed is:

1. Optoelectronic sensor device (08) arranged for recording of soiling on a cover (09) transparent for electromagnetic waves of a certain wavelength range, with at least one light source (12, 13) that emits at least two light beams (10, 11), a test surface (15) arranged in cover (09), having a concave surface (14) exposed to environmental effects, through which the light beams (10, 11) emerge and reenter, as well as at least one receiver (16, 17) that measures the radiation powers of the light beams (10, 11), on which the light beams (10, 11) are imaged independently of each other after reentry in an unsoiled surface (14), characterized by the fact that the test surface (15) has at least two areas (18, 19) with different microstructurings, in which a first microstructuring is designed, so that a liquid applied to the area (18) provided with the first microstructuring is held together drop-like, and a second microstructuring is designed, so that a liquid applied to the area (19) provided with the second microstructuring is distributed film-like, in which case, in the unsoiled state of surface (14), at least a first light beam (10) emerges and reenters through the first area (18) and at least a second light beam (11) emerges and reenters through the second area (19), so that a conclusion can be drawn concerning the transparency of the cover (09) exposed to soiling by evaluation of the radiation powers.

2. Optoelectronic sensor device according to claim 1, characterized by the fact that the light source emitting at least two light beams includes a device for beam widening and/or beam splitting.

3. Optoelectronic sensor device according to claim 1, characterized by the fact that the optoelectronic sensor device includes at least two light sources that each emit a light beam.

4. Optoelectronic sensor device according to claim 3, characterized by the fact that the at least one receiver (16, 17) that measures the radiation powers of the light beams (10, 11) includes a device for beam joining, as well as beams to distinguish the two light beams (10, 11).

5. Optoelectronic sensor device according to claim 3, characterized by the fact that the optoelectronic sensor device includes at least two receivers (16, 17), on which one light beam each is imaged.

6. Optoelectronic sensor device according to claim 5, characterized by the fact that the first microstructuring is designed as a smooth surface.

7. Optoelectronic sensor device according to claim 6, characterized by the fact that the second microstructuring is produced by a fine surface structure below the drop size that ordinarily forms on the material of the test surface (15) in liquid drops.

8. Optoelectronic sensor device according to claim 5, characterized by the fact that the first microstructuring is produced by a hydrophobic nanostructure and the second microstructuring by a hydrophilic nanostructure.

9. Optoelectronic sensor device according to claim 8, characterized by the fact that the microstructurings are produced by at least partial coating of the test surface (15).

10. Optoelectronic sensor device according to claim 5, characterized by the fact that microstructurings are produced by at least partial embossing of a fine surface structure.

11. Optoelectronic sensor device according to claim 10, characterized by the fact that the test surface is an integral component of the cover.

12. Optoelectronic sensor device according to claim 10, characterized by the fact that the test surface is part of a radiation conductor that can be integrated in cover (09).

13. Method for determination of transparency of soiling by a surface (14) exposed to environmental effects, transparent for electromagnetic waves of a certain wavelength range, characterized by the process steps:

Arrangement of at least two areas (18, 19) provided with different microstructurings on surface (14), in which a first microstructuring is designed, so that a liquid applied to the area (18) provided with the first microstructuring is held together drop-like, and a second microstructuring is designed, so that a liquid applied to the area (19) provided with the second microstructuring is distributed to a liquid film, Generation of at least two light beams (10, 11), at least a first one of which emerges and reenters through the first area, and at least a second of which emerges and reenters through the second area in the unsoiled state of surface (14), Measurement of the radiation powers of the light beams (10, 11) independently of each other, as well as Evaluation of the radiation powers of the two light beams (10, 11), in which the result of evaluation is an unsoiled surface (14), if, for both light beams (10, 11) an essentially unchanged radiation power is measured relative to an assigned start value and the result of the evaluation is a surface (14) wetted by a transparent liquid, if, for the first light beam (10), a reduced radiation power is measured relative to the assigned start value and, for the second light beam (11), a higher radiation power relative to the assigned start value is measured.

14. Method according to claim 13, characterized by the fact that a degree of transparency of the surface (14) is determined by independent comparison of the radiation powers of the two light beams (10, 11) with the characteristics that apply for the corresponding areas (18, 19).

15. Method according to claim 14, characterized by the fact that a conclusion concerning the soiling of a cover (09) connected to the surface is drawn by determination of soiling or transparency of surface (14).

* * * * *